(12) United States Patent
Vuorenmaa

(10) Patent No.: US 9,962,353 B2
(45) Date of Patent: May 8, 2018

(54) USE OF TALL OIL FATTY ACID IN BINDING TOXINS

(71) Applicant: Hankkija Oy, Hyvinkää (FI)

(72) Inventor: Juhani Vuorenmaa, Hyvinkää (FI)

(73) Assignee: Hankkija Oy, Hyvinkaa (FI)

( * ) Notice: Subject to any disclaimer, the term of this patent is extended or adjusted under 35 U.S.C. 154(b) by 0 days. days.

(21) Appl. No.: 15/027,493

(22) PCT Filed: Oct. 16, 2014

(86) PCT No.: PCT/FI2014/050783
§ 371 (c)(1),
(2) Date: Apr. 6, 2016

(87) PCT Pub. No.: WO2015/059350
PCT Pub. Date: Apr. 30, 2015

(65) Prior Publication Data
US 2016/0250171 A1    Sep. 1, 2016

(30) Foreign Application Priority Data

Oct. 24, 2013 (FI) .................................. 20136047

(51) Int. Cl.
| | | |
|---|---|---|
| A61K 31/20 | (2006.01) | |
| A23K 20/158 | (2016.01) | |
| A61K 36/13 | (2006.01) | |
| A61K 31/19 | (2006.01) | |
| A23L 5/20 | (2016.01) | |

(52) U.S. Cl.
CPC ............ *A61K 31/20* (2013.01); *A23K 20/158* (2016.05); *A23L 5/20* (2016.08); *A23L 5/273* (2016.08); *A61K 31/19* (2013.01); *A61K 36/13* (2013.01); *A23V 2002/00* (2013.01); *A61K 2236/00* (2013.01)

(58) Field of Classification Search
CPC .... A61K 31/201; A61K 36/13; A23K 20/158; A23L 1/0156; A23V 2002/00
USPC ........................................................ 514/558
See application file for complete search history.

(56) References Cited

U.S. PATENT DOCUMENTS

| | | |
|---|---|---|
| 2,240,365 A | 4/1941 | Dreger |
| 2,308,431 A | 1/1943 | Brandt |
| 2,423,236 A | 7/1947 | Harwood et al. |
| 2,481,356 A | 9/1949 | Segessemann et al. |
| 2,530,810 A | 11/1950 | Christenson et al. |
| 2,611,706 A | 9/1952 | Bernhart et al. |
| 2,736,663 A | 2/1956 | Weber |
| 2,854,420 A | 9/1958 | Clark et al. |
| 2,866,739 A | 12/1958 | Ciesielski et al. |
| 2,894,939 A | 7/1959 | Hampton |
| 2,941,941 A | 6/1960 | Groll |
| 2,987,183 A | 6/1961 | Bishop |
| 3,001,962 A | 9/1961 | Carlston |
| 3,009,820 A | 11/1962 | Gould |
| 3,066,160 A | 11/1962 | Hampton |
| 3,141,897 A | 7/1964 | Crecelius et al. |
| 3,175,916 A | 3/1965 | Costigliola et al. |
| 3,194,728 A | 7/1965 | Stump, Jr. |
| 3,257,438 A | 6/1966 | Wicke et al. |
| 3,311,561 A | 3/1967 | Anderson et al. |
| 3,458,625 A | 7/1969 | Ensor et al. |
| 3,691,211 A | 4/1972 | Julian |
| 3,830,789 A | 8/1974 | Garrett et al. |
| 3,887,537 A | 6/1975 | Harada et al. |
| 3,926,936 A | 12/1975 | Lehtinen |
| 4,000,271 A | 12/1976 | Kremer et al. |
| 4,076,700 A | 2/1978 | Harada et al. |
| 4,118,407 A | 10/1978 | Red et al. |
| 4,313,940 A * | 2/1982 | Pasarela ................ A01N 25/32 514/144 |
| 4,437,894 A | 3/1984 | Emerson |
| 4,443,437 A | 4/1984 | Prokosch et al. |
| 4,810,299 A | 3/1989 | Schilling et al. |
| 4,810,534 A | 3/1989 | Seaborne et al. |
| 5,428,072 A | 6/1995 | Cook et al. |
| 5,460,648 A | 10/1995 | Walloch et al. |
| 6,020,377 A | 2/2000 | O'Quinn et al. |
| 6,229,031 B1 | 5/2001 | Strohmaier et al. |
| 6,608,222 B2 | 8/2003 | Bonsignore et al. |
| 8,741,171 B2 | 6/2014 | Swift et al. |
| 9,358,218 B2 | 6/2016 | Vuorenmaa et al. |
| 9,422,057 B2 | 8/2016 | Hamunen |
| 2002/0147356 A1 | 10/2002 | Bonsignore et al. |
| 2002/0183298 A1 | 12/2002 | Schersl et al. |
| 2003/0144536 A1 | 7/2003 | Sonnier et al. |
| 2005/0107582 A1 | 5/2005 | Wong et al. |
| 2005/0203279 A1 | 9/2005 | Rojas et al. |
| 2006/0021276 A1 | 2/2006 | Sonnier |

(Continued)

FOREIGN PATENT DOCUMENTS

| | | |
|---|---|---|
| CA | 2 107 647 A1 | 4/1994 |
| CN | 101461443 A | 6/2009 |

(Continued)

OTHER PUBLICATIONS

International Search Report for International Patent Application No. PCT/2014/050783 dated Dec. 23, 2014.
Finnish Search Report for Finnish Patent Application No. 20136047 dated Jul. 2, 2014.
Huwig, A. et al., "Mycotoxin detoxication of animal feed by different adsorbents", *Toxicology Letters*, 122: 179-188 (2001).
Magee, T. et al., "Composition of American Distilled Tall Oils", *JAOCS*, 69(4): 321-324 (1992).
Shetty, P. et al., "*Saccharomyces cerevisiae* and lactic acid bacteria as potential mycotoxin decontaminating agents", *Trends in Food Science & Technology*, 17: 48-55 (2006).
"Explanatory Notes to the Harmonized Commodity Description and Coding System", The Department of Duty Collection of the 25 General Administration of Customs, China Commerce and TradePress, published on Jan. 31, 2007, see p. 478: "Tall Oil, Whether or Not Refined". English translation of relevant parts.

(Continued)

*Primary Examiner* — Yong Chu
(74) *Attorney, Agent, or Firm* — Merchant & Gould P.C.

(57) ABSTRACT

The present invention relates to use of a tall oil fatty acid and/or a tall oil fatty acid which is modified by saponification in binding toxins.

11 Claims, 2 Drawing Sheets

(56) References Cited

U.S. PATENT DOCUMENTS

Figure 1A:
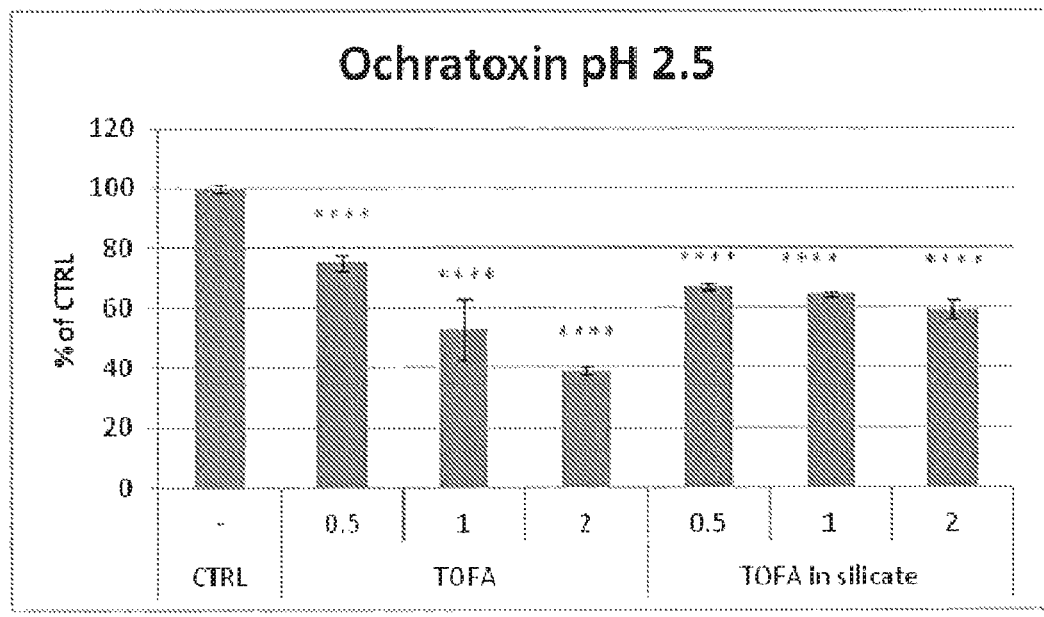

| | | |
|---|---|---|
| 2006/0286185 A1 | 12/2006 | Prokosch |
| 2008/0262251 A1 | 10/2008 | Sato et al. |
| 2009/0012164 A1 | 1/2009 | Kelderman |
| 2009/0220638 A1* | 9/2009 | Pablos Perez .......... C11C 1/025 426/2 |
| 2009/0277972 A1 | 11/2009 | Kennon et al. |
| 2009/0285931 A1 | 11/2009 | Shelby et al. |
| 2009/0297687 A1 | 12/2009 | Ramirez Marco et al. |
| 2011/0081442 A1 | 4/2011 | Weill et al. |
| 2011/0200570 A1 | 8/2011 | Mosbaugh et al. |
| 2011/0212217 A1 | 9/2011 | Herranen et al. |
| 2011/0212218 A1 | 9/2011 | Herranen et al. |
| 2012/0070516 A1 | 3/2012 | Tranquil et al. |
| 2013/0041192 A1 | 2/2013 | Saviainen et al. |
| 2015/0164966 A1 | 6/2015 | Vuorenmaa et al. |
| 2015/0238454 A1 | 8/2015 | Vuorenmaa et al. |
| 2016/0081368 A1 | 3/2016 | Vuorenmaa et al. |
| 2016/0081952 A1 | 3/2016 | Vuorenmaa et al. |
| 2016/0089407 A1 | 3/2016 | Vuorenmaa et al. |
| 2016/0250269 A1 | 9/2016 | Rintola et al. |

FOREIGN PATENT DOCUMENTS

| | | |
|---|---|---|
| DE | 101 06 078 A1 | 9/2002 |
| EP | 0 078 152 A1 | 5/1983 |
| EP | 0 146 738 A2 | 7/1985 |
| EP | 1 586 624 A1 | 10/2005 |
| EP | 2 343 061 A1 | 7/2011 |
| FI | 41337 B | 6/1969 |
| FI | 20110371 A | 4/2013 |
| FI | 20120287 A | 4/2013 |
| GB | 955 316 A | 4/1964 |
| GB | 2 139 868 A | 11/1984 |
| GB | 2 271 282 A | 4/1994 |
| JP | S60-237008 A | 11/1985 |
| WO | WO 94/16690 A1 | 8/1994 |
| WO | WO 99/10148 A1 | 3/1999 |
| WO | WO 02/02106 A1 | 1/2002 |
| WO | WO 03/024681 A1 | 3/2003 |
| WO | WO 2006/040537 A1 | 4/2006 |
| WO | WO 2008/099051 A2 | 8/2008 |
| WO | WO 2008/154522 1 | 12/2008 |
| WO | WO 2009/079680 A1 | 7/2009 |
| WO | WO 2009/106696 A1 | 9/2009 |
| WO | WO 2011/042613 A2 | 4/2011 |
| WO | WO 2011/055018 A2 | 5/2011 |
| WO | WO 2011/080399 A1 | 7/2011 |
| WO | WO 2011/099000 A2 | 8/2011 |
| WO | WO 2012/037297 A1 | 3/2012 |
| WO | WO 2013/060936 A1 | 5/2013 |
| WO | WO 2013/118099 A1 | 8/2013 |
| WO | WO 2013/171370 A1 | 11/2013 |
| WO | WO 2014/184430 A1 | 11/2014 |

OTHER PUBLICATIONS

Extended European Search Report for corresponding European Patent Application No. 14856137.6 dated Apr. 4, 2017, 5 pgs.

"Carboxylic Acids, Fatty Acids from Tall Oil", Kirk-Othmer Encyclopedia of Chemical Technology, Copyright 1999-2014 by John Wiley and Sons, Inc., 4 pgs.

Antila, M. et al., "The fatty acids of tall oil and their ethyl and glyceryl esters as animal fodder ingredients, the chemical and physical properties of the fatty acid fraction and esters prepared from this fraction", Journal ACTA Agricultureae Scandinavia, 12: 95-105, 1962, Abstract.

Bannink, A. et al., "A model of enteric fermentation in dairy cows to estimate methane emission for the Dutch National Inventory Report using the IPCC Tier 3 approach", 166-167: 603-618, 2011.

Beauchemic, K.A., et al., "Nutritional management for enteric methane abatement: a review", Australian Journal of Experimental Agriculture, 48: 21-27, 2008.

de Graaf et al., "Consumption of tall oil-derived phytosterols in a chocolate matrix significantly decreases plasma total and low-density lipoprotein-cholesterol levels", British Journal of Nutrition, 88: 479-488, 2002.

Grainger, C. et al., "Can enteric methane emissions from ruminants be lowered without lowering their production?", Animal Feed Science and Technology, 166-167: 308-320, 2011.

Machmüller, A., "Medium-chain fatty acids and their potential to reduce methanogenesis in domestic ruminants", Agriculture, Ecosystems and Environment, 112: 107-114, 2006.

Machmüller, A. et al., "Potential of various fatty feeds to reduce methane release from rumen fermentation in vitro (Rusitec)", Animal Feed Science Technology, 71: 117-130, 1998.

McGuire, J. et al., "Gas Chromatographic Analysis of Tall Oil Fractionation Products After Methylation with N,N-Dimethylformamide Dimethylacetal", Journal of Chromatographic Science, 36: 104-108, 1998.

Norlin, L. "Tall Oil", Ullmann's Encyclopedia of Industrial Chemistry, published online: Jun. 15, 2000.

O'Quinn, P.R. et al., "Effects of modified tall oil and creatine monohydrate on growth performance, carcass characteristics, and meat quality of growing-finishing pigs", Journal of Animal Science, 78(9): 2376-2382, 2000.

O'Quinn, P.R. et al., "Effects of modified tall oil versus conjugated linoleic acid on finishing pig growth performance and carcass characteristics", KSU Swine Day, 157-161, 1998.

O'Quinn, P.R. et al., "Effects of modified tall oil versus a commercial source of conjugated linoleic acid and increasing levels of modified tall oil on growth performance and carcass characteristics of growing-finishing pigs", Journal of Animal Science, 78(9): 2359-2368, 2000.

Patra, A.K., "Effects of Essential Oils on Rumen Fermentation, Microbial Ecology and Ruminant Production", Asian Journal of Animal and Veterinary Advances, 6(5): 416-428, 2011.

Polan, C.E. et al., "Biohydrogenation of Unsaturated Fatty Acids by Rumen Bacteria", Journal of Bacteriology, 88(4): 1056-1064, 1964.

Product Data Sheet SYLFAT® 2LTC tall oil fatty acid [online], Arizona Chemical, [last modified Jul. 20, 2009], retrieved Feb. 20, 2013, URL: http://www.arizonachemical.com/Global/PDS/EU_product_data_sheets/SYLFAT%C2%AE%202LTC.pdf.

Savluchinske-Feio, S. et al., "Antimicrobial activity of resin acid derivatives", Applied microbiology and Biotechnology, 72(3): 430-436, 2006.

Smith, E., et al., "Isopimaric Acid from Pinus nigra shows Activity against Multi-drug-resistant and EMRSA Strains for Staphylococcus aureus", Phytotherapy Research, 19(6): 538-542, 2005.

Snell, F. et al., "Comparative Value of Fatty Acids and Resin Acids of Tall Oil in Soaps", The Journal of the American Oil Chemist's Society, 27(8): 289-295, 1950.

Zhou, X. et al., "The Effect of Saturated Fatty Acids on Methanogenesis and Cell Viability of Methanobrevibacter ruminantium", Archaea, 2013: 1-9, 2013.

Duncan, D.P., "Tall Oil Fatty Acids", Naval Stores, 346-349 (1989).

Gudmundur, B. et al., "Antibacterial, Antiviril and Antifungal Activities of Lipids" in "Lipids and Essential Oils as Antimicrobial Agents", John Wiley & Sons, 47-80 (2011).

Van Nevel, C.J. et al., "Effect of Fatty Acid Derivatives on Rumen Methane and Propionate In Vitro", Applied Microbiology, 365-366 (1971).

* cited by examiner

USE OF TALL OIL FATTY ACID IN BINDING TOXINS

This application is a National Stage Application of PCT/FI2014/050783, filed 16 Oct. 2014, which claims benefit of Serial No. 20136047, filed 24 Oct. 2013 in Finland and which applications are incorporated herein by reference. To the extent appropriate, a claim of priority is made to each of the above disclosed applications.

FIELD OF THE INVENTION

The invention relates to use of a tall oil fatty acid and/or a tall oil fatty acid which is modified by saponification in binding toxins.

BACKGROUND OF THE INVENTION

Toxins are poisonous substances produced within living cells or organisms. Toxins such as mycotoxins are a chemically variable group of secondary metabolites of fungi, which can be found in grains and other feedstuffs even in the absence of any visible fungal growth. High temperature and air humidity during the storage increase the likelihood of fungal growth, but mycotoxin contamination can also occur already in the field. Visible appearance or smell of grains or silage does not indicate the presence or absence of mycotoxin contamination. Effects of toxins such as mycotoxins to farm animals are very variable, and range from increased mortality to decreased fertility and performance. Mycotoxins may also disturb the immune system of animals and make them more susceptible to diseases.

Due to the chemical variability of mycotoxins, analysis of all feedlots for even the most common mycotoxins would be too expensive. Therefore mycotoxin adsorbents are often used to give extra insurance against mycotoxin contamination in feeds. Mycotoxin adsorbents are substances that are itself not digested or absorbed by the animal. They are assumed to bind toxins during the passage through the alimentary canal. Thus, instead of being absorbed by the animals, the toxins get eventually voided via feces.

Toxin binders can also adsorb other types of toxins, like bacterial toxins or secondary metabolites of plants from the digestive tract. Activated carbon (charcoal), which is a fine-granulated powder with a porous microstructure, is an efficient toxin binder. It is a recommended general toxin binder in various poisonings. However, charcoal also binds vitamins and minerals, which makes it unsuitable for continuous use in feeds. Silicate clays are also used as adsorbents in feeds.

Fractional distillation of crude tall oil, obtained as a by-product of the Kraft process of wood pulp manufacture, produces distilled tall oil (DTO) which typically comprises over 10% resin acids and less than 90% fatty acids. Further refinement of distilled tall oil produces the tall oil fatty acid (TOFA), which is available in a variety of compositions differing in the fatty acids and resin acids content. Because the TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

PURPOSE OF THE INVENTION

The purpose of the invention is to provide a new type of absorbent for use in binding toxins.

SUMMARY

Use of a tall oil fatty acid and/or a tall oil fatty acid which is modified by saponification according to the present invention is characterized by what is presented in claim 1.

DETAILED DESCRIPTION OF THE INVENTION

FIG. 1*a* Reduction of free ochratoxin A from the aqueous medium by the saponified TOFA.

FIG. 1*b* Reduction of free zearalenone from the aqueous medium by the saponified TOFA.

FIG. 2*a* The relative amount of ochratoxin A in the intestinal tissue of rat as a response to the saponified TOFA.

FIG. 2*b* The relative amount of zearalenone in the intestinal tissue of rat as a response to the saponified TOFA.

The present invention is based on the realization that the tall oil fatty acid and the modified tall oil fatty acid can be used in binding toxins.

The term "tall oil fatty acid" or "TOFA" should be understood as referring to a composition obtained by distillation of crude tall oil and further refinement of distilled tall oil. The TOFA or the TOFA which is modified by saponification typically comprises 90-98% (w/w) fatty acids. Further, the TOFA or the TOFA which is modified by saponification may comprise 1-10% (w/w) resin acids.

Resin acids are known to have antimicrobial, including antibacterial, properties. The present inventors have found that resin acids of TOFA are not absorbable, and they have potential in toxin binding.

In this context, the term "toxin" should be understood as referring to any poisonous substance produced within living cells or organisms. Toxins are products of plants, animals, microorganisms, for example bacteria, viruses, fungi, rickettsiae, protozoa, etc. In this context, the term "mycotoxin" should be understood as referring to a toxic secondary metabolite produced by fungi, such as yeast and mould. The most common mycotoxins in grains or silage are for example aflatoxins, zearalenone, ochratoxin A, deoxynivalenol, fumonisin and T-2 toxin. The toxins will vary depending on environmental factors.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In one embodiment of the present invention, the tall oil fatty acid which is modified by saponification comprises 1-10% (w/w) of resin acids.

In one embodiment of the present invention, the tall oil fatty acid which is modified by saponification comprises 2-9% (w/w) resin acids.

In one embodiment of the present invention, the tall oil fatty acid which is modified by saponification comprises 5-9% (w/w) resin acids.

In one embodiment of the present invention, the tall oil fatty acid comprises 1-10% (w/w) of resin acids.

In one embodiment of the present invention, the tall oil fatty acid comprises 2-9% (w/w) resin acids.

In one embodiment of the present invention, the tall oil fatty acid comprises 5-9% (w/w) resin acids.

In this context, the term "resin acids" should be understood as referring to a complex mixture of various acidic compounds comprised by tall oil which share the same basic skeleton including a threefused ring. The exact composition of the resin acids present in the TOFA varies e.g. according to the species of the trees the TOFA is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In one embodiment of the present invention, the tall oil fatty acid which is modified by saponification comprises 90-98% (w/w) of fatty acids.

In one embodiment of the present invention, the tall oil fatty acid comprises 90-98% (w/w) of fatty acids.

Various processes for the saponification of the TOFA using e.g. NaOH or CaOH are known to a person skilled in the art.

In one embodiment of the present invention, the TOFA which is modified by saponification, the TOFA soap, is dried. The modified TOFA can be dried by spray drying, drum drying or by any other known suitable drying method.

The tall oil fatty acid or the tall oil fatty acid which is modified by saponification can be used as a feed additive which is effective in binding toxins.

In one embodiment of the present invention, the tall oil fatty acid which is modified by saponification is used together with silicate carrier.

In this context, the term "feed additive" should be understood as referring to a composition that may be added to a feed or used as such in the feeding of animals. The feed additive may comprise different active ingredients. The feed additive may be added in the feed in a concentration of 0.1-5 kg/ton of dry weight, preferably 0.2-3 kg/ton, most preferably 0.5-2 kg/ton of the dry weight of the total amount of the feed. The TOFA or the TOFA which is modified by saponification or the feed additive comprising the TOFA or the TOFA which is modified by saponification according to the invention may be added to the feed or feed additive as such, or it may in general be further processed as desired. Further, it may be added to the feed or feed additive, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

In one embodiment of the present invention, the feed additive comprises the TOFA which is modified by saponification and which is absorbed into a carrier material suitable for the feed composition such as sugarbeet pulp.

In one embodiment of the present invention, the feed additive comprises the TOFA which is absorbed into a carrier material suitable for the feed composition such as sugarbeet pulp.

In one embodiment of the present invention, the feed additive comprises the TOFA which is modified by saponification and which is dried.

The feed composition can comprise the TOFA which is modified by saponification or the feed additive comprising the TOFA which is modified by saponification according to the invention in an amount of 0.01-0.5% (w/w), preferably 0.02-0.3% (w/w), most preferably 0.05-0.2% (w/w) of the dry weight of the total amount of the feed.

In one embodiment of the present invention, the feed composition comprises the TOFA or the feed additive comprising the TOFA in an amount of 0.01-0.5% (w/w), preferably 0.02-0.3% (w/w), most preferably 0.05-0.2% (w/w) of the dry weight of the total amount of the feed.

The modified tall oil fatty acid according to the invention is produced by saponification. The method comprises the steps of adding a base to an aqueous TOFA solution and heating the mixture. The mixture is stirred during the heating step. The mixture is heated at a temperature of 80-120° C., preferably at 85-95° C., for a period of 1-3 hours, preferably for 2 hours.

Any base suitable for saponification, such as an alkali metal hydroxide, can be used as the base. Normally, the base that is used is a sodium or potassium hydroxide.

In one embodiment of the present invention, the method of producing a modified tall oil fatty acid further comprises a step of drying. The drying can be carried out by spray drying, drum drying or by any other known drying method.

In one embodiment of the present invention, the TOFA which is modified by saponification is administered to an animal in an effective amount.

In one embodiment of the present invention, the TOFA is administered to an animal in an effective amount.

The present invention has a number of advantages. The TOFA is a readily available, natural, low-cost and environmentally friendly material. Further, it is non-toxic and well tolerated. The invention is effective in absorbing toxins. Subsequently, other benefits of the invention are e.g. improved animal health and productivity.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

Test A: Toxin Adsorption into Solid Phase In Vitro

The capacity of a test product to remove toxins from aqueous medium was measured in this test. An efficient toxin adsorbent should be able to bind the toxin in all compartments of the digestive tract, to inhibit the toxin from getting absorbed by the animal. To evaluate the efficacy of the binder in the acidic stomach, the test was run at pH value 2.5 (50 mM glycine-HCl buffer).

The test product was a saponified Tall Oil Fatty Acid (TOFA) product which contains 8.5% resin acids. The saponified TOFA was manufactured by adding 140 mg of NaOH (sodium hydroxide) to 1 gram of TOFA, adding enough water to adjust the total dry matter (TOFA) percentage of the mixture to 18-20%, heating the mixture to +90° C., keeping the temperature at +90° C. for 120 minutes, during which time the mixture was gently stirred at 15 min intervals. The product tested was the saponified TOFA (8.5%) with or without silicate carrier.

The test A was conducted with two toxins Ochratoxin A (OTA) and Zearalenone (ZEA), at pH-value 2.5, three test substance levels 0.5, 1 and 2 kg/ton and four replicate samples per treatment. Control treatment was replicated 8 times.

Mycotoxins OTA and ZEA were available as 3H-labeled pure compounds, and radioactivity, measured by liquid scintillation counting, was used for their quantification in the samples.

The experiment was conducted in silanized glass vials in 1 ml volume of buffer. In the test system, the bound radioactive toxin becomes removed from the liquid phase through co-pelleting with the insoluble components of the potential binder. The following procedure was used: 1. The test products were weighed into the vials, 2. 3H-labeled and intact mycotoxin was mixed with the buffers to get the final toxin concentration of 10 μg/l, 3. 1 ml of the buffer-mycotoxin solution was added to the vials, 4. The vials were sealed and kept for 2 hours at 37° C. in constant slow shaking, 5. The vials were centrifuged for 10 min at 3000×g 6. 50 μl of the supernatant was mixed with 150 μl of liquid scintillation cocktail (Optiphase) into wells of a 96-well microtiter plate and 7. The radioactivity of the samples was measured with a liquid scintillation counter for five minutes.

Results

Figure 1B:
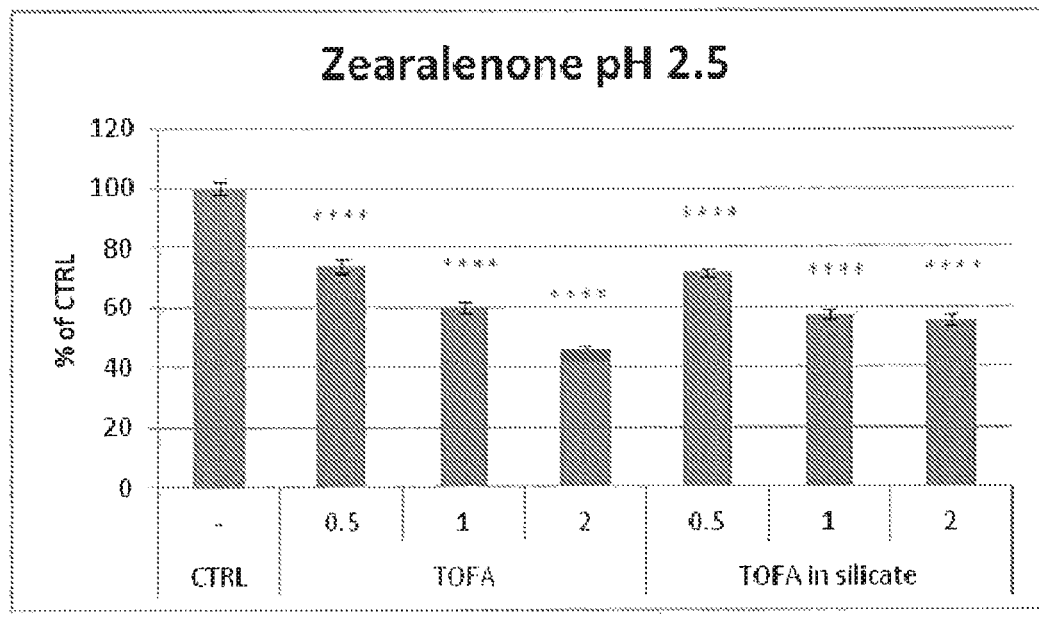

The results are illustrated in FIGS. 1a and 1b. The saponified TOFA was able to bind OTA from the aqueous medium statistically significantly, and the binding was dependent on the concentration of the test product (FIG. 1a). The saponified TOFA adsorbed 25-60% of the free OTA from the medium.

The saponified TOFA significantly decreased the amount of free ZEA even at the lowest dosages ($p<0.001$; FIG. 1b). The saponified TOFA removed approximately 30-60% of the free toxin.

In some cases the silicate carrier may be a beneficial addition to the combination of the saponified TOFA, in order to increase the range of toxins to which the product combination is effective.

Example 2

Test B: Inhibition of Toxin Uptake Ex Vivo

This test studied the ability of the saponified TOFA to inhibit the uptake of toxins Ochratoxin A (OTA) and Zearalenone (ZEA) into live intestinal tissue of a rat ex vivo.

The saponified TOFA comprising 8.5% resin acids was manufactured as described in Example 1. The saponified TOFA was tested with silicate carrier.

The test B was conducted with two toxins Ochratoxin A (OTA) and Zearalenone (ZEA), two test substance levels 1 and 2 kg/ton and three replicate samples per treatment. Control treatment was replicated 6 times.

The rats were not exposed to mycotoxins prior to the experiment.

The test was conducted as follows for the mycotoxins: 1. The ileum of euthanized rat was immediately removed, opened, emptied and rinsed with a physiological, buffered saline solution (128 mM NaCl, 4.7 mM KCl, 2.5 mM CaCl2, 1.2 mM KH2PO4, 2.6 mM MgSO4, 2.0 mM NaHCO3, pH 7.3), 2. The ileum was cut into transverse 2-mm slices and kept in the saline solution until the incubations. Peyer's patches were removed, 3. The slices were immersed in the same basal saline solution amended with the radioactively labeled mycotoxin (10 μg/l), and with or without saponified TOFA, 4. After 5 min incubation at room temperature, the slices were quickly (2-3 seconds) rinsed with the same saline solution without the toxin or test substances, 5. Excess saline was removed, 6. The slices were placed in pre-weighed 3-ml liquid scintillation vials, and reweighed to calculate their mass, 7. 0.25 ml of tissue solvent was added to solubilize the tissue slices overnight at room temperature, 8. 2.5 ml of liquid scintillation cocktail was added to the vials after the slices were fully dissolved into the solubilizer, 9. The radioactivity of the slices was calculated with a liquid scintillation counter and 10. The radioactivity per unit mass in the treatments was compared against of the control treatment.

Results

Figure 2A:
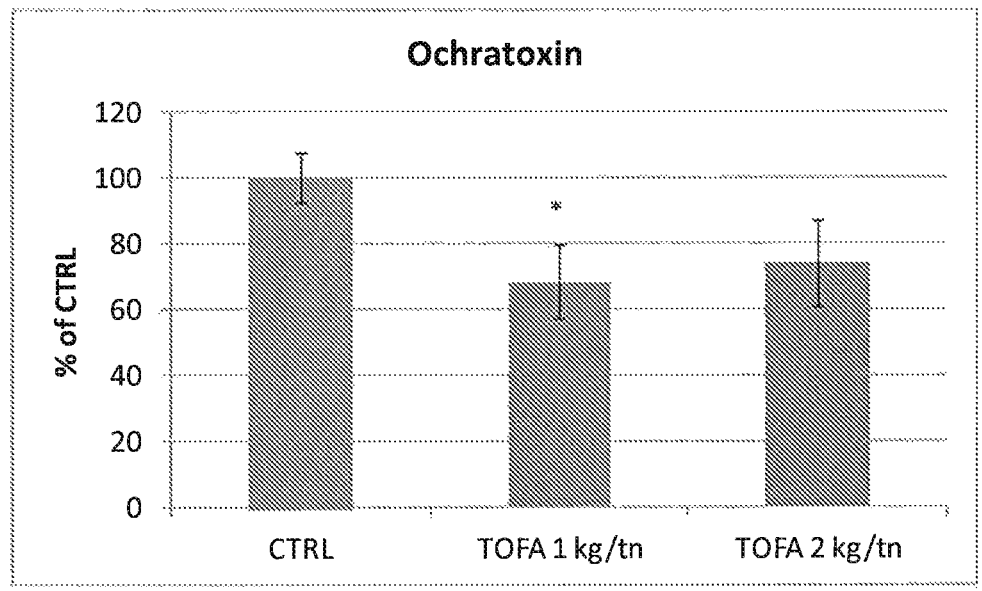
Figure 2B:
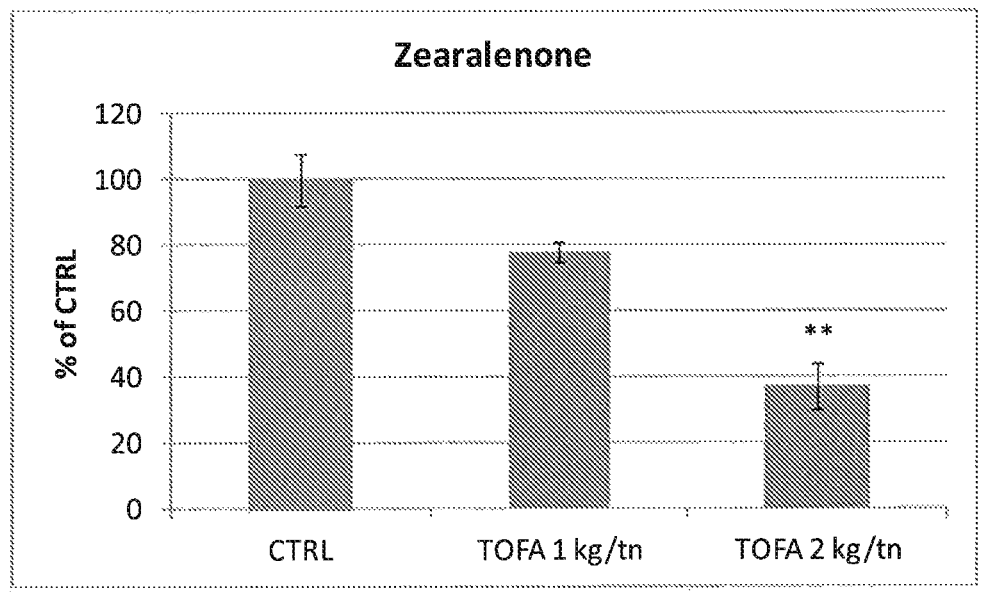

The results are illustrated in FIGS. 2a and 2b. The results were expressed in relation to the control treatment without binders. Treatment values less than 100% indicate inhibition of toxin uptake by the test product. The saponified TOFA decreased the uptake of OTA ($p<0.05$ for the 1 kg/tn treatment) (FIG. 2a). The saponified TOFA dose-dependently decreased the uptake of ZEA ($p<0.01$ for the 2 kg/tn treatment) (FIG. 2b). These results show that the saponified TOFA is an efficient agent for toxin binding in the ex vivo model with the presence of live intestinal tissue.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method of binding toxins comprising:
   administering tall oil fatty acid comprising 1-10% (w/w) resin acids or tall oil fatty acid modified by saponification comprising 1-10% (w/w) resin acids to an animal; and
   allowing the tall oil fatty acid comprising 1-10% (w/w) resin acids or the tall oil fatty acid modified by saponification comprising 1-10% (w/w) resin acids to bind with toxins during passage through the alimentary canal.

2. A method according to claim 1, wherein the method comprises:
   administering the tall oil fatty acid comprising 1-10% (w/w) resin acids modified by saponification to the animal.

3. A method according to claim 1 comprising:
   administering the tall oil fatty acid comprising 1-10% (w/w) resin acids to the animal.

4. A method according to claim 1, wherein the toxin is mycotoxin.

5. A method according to claim 1, wherein the tall oil fatty acid or the tall oil fatty acid modified by saponification comprises 2-9% (w/w) resin acids.

6. A method according to claim 1, wherein the tall oil fatty acid or the tall oil fatty acid modified by saponification comprises 5-9% (w/w) resin acids.

7. A method according to claim 1, wherein the tall oil fatty acid or the tall oil fatty acid which is modified by saponification comprises 91-98% (w/w) fatty acids.

8. A method according to claim 1, wherein the tall oil fatty acid or the tall oil fatty acid modified by saponification is dried.

9. A method according to claim 1, wherein the tall oil fatty acid comprising 1-10% (w/w) resin acids or the tall oil fatty acid modified by saponification comprising 1-10% (w/w) resin acids is administered to an animal together with the feed composition.

10. A method according to claim 1, wherein the tall oil fatty acid comprising 1-10% (w/w) resin acids or tall oil fatty acid modified by saponification comprising 1-10% (w/w) resin acids binds with the toxins in all compartments of the digestive tract.

11. A method according to claim 1, wherein the tall oil fatty acid comprising 1-10% (w/w) resin acids or tall oil fatty acid modified by saponification comprising 1-10% (w/w) resin acids inhibits the toxins from getting absorbed by the animal.

* * * * *